Figure 1:
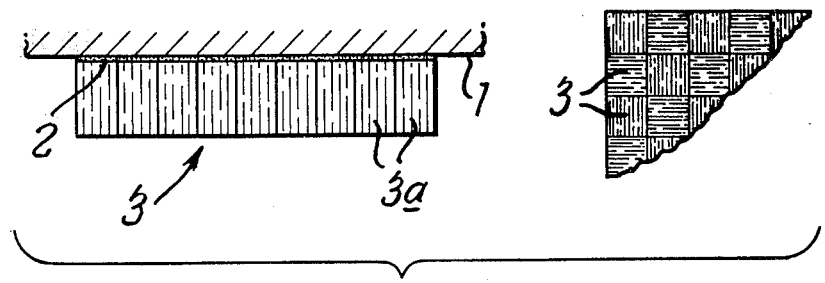

United States Patent [19]

Davis et al.

[11] 4,324,602

[45] * Apr. 13, 1982

[54] METHOD FOR REDUCING THE THERMAL INERTIA OF FURNACE OR OVEN WALLS

[75] Inventors: Richard P. B. Davis; Harold G. Emblem; Richard D. Shaw; Stanley J. Shelley, all of Bromley, England

[73] Assignee: Zirconal Processes Limited, Bromley, England

[ * ] Notice: The portion of the term of this patent subsequent to Mar. 18, 1997, has been disclaimed.

[21] Appl. No.: 216,871

[22] Filed: Dec. 15, 1980

Related U.S. Application Data

[60] Continuation of Ser. No. 129,818, Mar. 12, 1980, abandoned, which is a continuation of Ser. No. 804,079, Jun. 6, 1977, Pat. No. 4,194,036, which is a division of Ser. No. 707,108, Jul. 20, 1976, abandoned.

[30] Foreign Application Priority Data

Jul. 29, 1975 [GB] United Kingdom ............... 31736/75
Nov. 28, 1975 [GB] United Kingdom ............... 49043/75

[51] Int. Cl.³ .................... B32B 31/26; E04F 13/00; F27D 1/16
[52] U.S. Cl. ....................................... 156/71; 52/227; 52/506; 52/747; 156/73.1; 156/83; 156/155; 156/191; 156/275.5; 264/30; 428/281; 266/285; 428/74; 428/76; 428/114; 428/119; 428/255; 428/902; 428/920

[58] Field of Search ................. 52/227, 404, 506, 509, 52/747; 156/62.2, 62.8, 71, 83, 94, 155, 272, 73.1, 191; 264/30; 266/280, 281, 285, 286; 428/74, 76, 114, 119, 255, 902, 920; 432/76

[56] References Cited

U.S. PATENT DOCUMENTS

| | | | |
|---|---|---|---|
| 2,546,230 | 3/1951 | Modigliani | 428/108 |
| 2,949,953 | 8/1960 | DiMaio et al. | 138/149 |
| 3,012,923 | 12/1961 | Slayter | 156/62.2 |
| 3,135,297 | 6/1964 | Nordberg et al. | 138/144 |
| 3,819,468 | 6/1974 | Sauder et al. | 156/71 X |
| 3,832,815 | 9/1974 | Balaz et al. | 52/227 |
| 3,854,262 | 12/1974 | Brady | 52/404 |
| 3,892,396 | 7/1975 | Monaghan | 52/506 X |
| 3,930,916 | 1/1976 | Shelley | 156/71 |
| 3,993,237 | 11/1976 | Sauder et al. | 156/71 X |
| 4,001,996 | 1/1977 | Byrd | 52/509 |
| 4,086,737 | 5/1978 | Byrd | 52/227 |
| 4,120,641 | 10/1978 | Myles | 264/30 X |
| 4,123,886 | 11/1978 | Byrd | 52/509 |
| 4,194,036 | 3/1980 | Davis et al. | 428/74 |

FOREIGN PATENT DOCUMENTS 90219 3/1961 Denmark .
72983 1/1948 Norway .

Primary Examiner—Edward C. Kimlin
Assistant Examiner—Robert A. Dawson
Attorney, Agent, or Firm—Sprung, Felfe, Horn, Lynch & Kramer

[57] ABSTRACT

The invention relates to reducing the thermal inertia of furnace or oven walls. Insulating modules under compression are secured to the wall and released from compression upon firing of the furnace.

15 Claims, 10 Drawing Figures

METHOD FOR REDUCING THE THERMAL INERTIA OF FURNACE OR OVEN WALLS

RELATED APPLICATIONS

This application is a continuation of application Ser. No. 129,818 filed Mar. 12, 1980, now abandoned, which is a continuation of application Ser. No. 804,079 filed June 6, 1977, now U.S. Pat. No. 4,194,036 issued Mar. 18, 1980, which in turn is a division of application Ser. No. 707,108 filed July 20, 1976, now abandoned.

This invention relates to the modular construction of furnaces, that is to say, the construction of the internal wall of a furnace from discrete relatively small modules of refractory material. The invention is concerned both with the structural and insulating modules which are attached to the cold face of a furnace, i.e., to the basic metal construction of the furnace itself and to purely insulating and refractory modules, hereinafter referred to as "biscuits", which are secured to an existing hot face made up, for example, of refractory bricks. In the latter case, the invention envisages reducing the thermal inertia, i.e., the amount of heat required to raise the walls of the furnace to operating temperature by the application of light highly refractory "biscuits".

In the modular construction of furnace walls it has been proposed to secure each module to the basic metal furnace wall construction, the "cold face", or to the hot face of refractory bricks by some physical means such as, for example, brackets or rivets.

According to the present invention the surface of the module which is to be fixed to the furnace hot or cold face is tacky, i.e., when applied to an inclined or overhanging surface, it provides sufficient adhesion not to fall under gravity. Further, according to the invention, after application the tacky surface is caused or allowed to set into a stable heat resistant and refractory condition which firmly and permanently adheres to the furnace wall. The present invention envisages several means for achieving this setting:

Firstly, the invention provides what may be broadly described as a chemical procedure, wherein the tacky rear surface layer is contacted with a reagent, either before or after application to the furnace wall, which causes it to set. This can be achieved by mixing a self-setting cement, applying it to the back of the module and placing the module on the wall and allowing the cement to set. The setting can be accelerated by preheating the furnace face. Alternatively the module can be coated with a cement which immediately prior to placing the module is treated with a setting agent.

An alternative procedure envisaged is to apply the tacky module to the hot or cold face and subsequently to cause setting by introducing the setting agent. This can be achieved by contacting the module as a whole with a gas vapour or mist of liquid droplets and allowing the gas vapour or mist to impregnate the module and react with the rear surface. The setting agent can, as an alternative, be introduced by injection through the module. Refractory binder techniques wherein a binder is hardened by an accelerator can thus be employed, the binder being used to impregnate the module or module part and the accelerator applied by injection or as a gas, vapour or mist. Thus in an embodiment an alkaline alkali metal silicate system with a suitable refractory filler providing an adhesive cement, is hardened by contracting the cement with an acid or an acid-producing gas such as carbon dioxide, sulphur dioxide or hydrogen-chloride. In a further possible system a cement comprising as the active ingredient an aluminium hydroxyhalide is hardened by contacting it with ammonia or an amino-alcohol. Thus the invention provides alkali cements hardened by acids, and acidic cements hardenable by alkalis. In these preferred techniques the module can be applied by a suitable applicator which embraces the module closely and is connectable to a source of gas, vapour or mist. In the case of injection a tool having generally similar dimensions to the module has a plurality of injection nozzles on the front face and a connection to a source of liquid. Such a tool enables liquid to be injected through the module to contact substantially the whole rear tacky face.

The invention also envisages hardening a tacky cement by some physical technique such as electrical, microwave or ultrasonic energy applied by appropriate electrodes. In an embodiment an aluminium heating element is provided under the tacky layer. An energising device has conductive probes which can be inserted through the module to make electrical contact with the heating element. The heating element can thus be energised from the front of the module to set the cement. These techniques are a development of the simple warming techniques referred to previously. A further possibility is to set a tacky cement by injection from the front of the module of a desiccating agent such as silica gel.

Although the invention is applicable to modules of any appropriate refractory composition it finds particular application to modules which consist of or comprise fibres orientated so that the fibres are at right angles to the plane of the module and end-on to the furnace wall.

The choice of fibre will be determined by the specified operating temperatures of the furnace. Thus for temperatures of up to 900° C. mineral wool fibres may be used, for temperatures between 900° C. and 1200° C. aluminosilicate ceramic fibres will normally be used whilst for temperatures between 1200° C. and 1600° C. alumina fibres should be used.

In the case of a module made up of "end-on" fibres the fibres do not have sufficient coherence to accept readily an adhesive coating.

The present invention thus proposes wrapping a biscuit, preferably made up of end-on fibres, with combustible netting thereby rendering the biscuit coatable with an adhesive. The netting is held in position with glue applied to the faces of the biscuits, the glue usually being organic and having sufficient strength to provide, with the netting, a tough flexible outer skin. The mesh of the netting should be sufficiently small to ensure the physical integrity of the module and sufficiently large to allow effective contacting of the fibres with cement. A $\frac{1}{8}"$—$\frac{1}{4}"$ mesh has been found effective. Upon first firing of the furnace the netting is burnt away. If the fibres are held in elastic compression recovery on burning off the mesh causes each module to press against adjacent module(s) thereby enhancing the coherence of the wall as a whole. A further advantage of the netting wrap is that, when applying adhesive cement with a bladed tool, such as a trowel, the tool blade can readily be wiped clean of adhesive on the netting.

In embodiments of the invention wherein the combustible netting is not being used some other combustible means will preferably be provided for holding the module in elastic compression.

The invention contemplates insulating modules formed of one or a plurality of insulating layers. Also a module with a flexible or a rigid backing.

The present invention further provides a circular biscuit formed by winding a strip or strips of "end-on" fibres into a spiral. The circular biscuit thus formed is bound into position with a combustible netting, the netting being held in position with radial strips of glue. Large circular pieces fabricated in this way may be cut into sections and re-assembled on installation.

Figure 2:
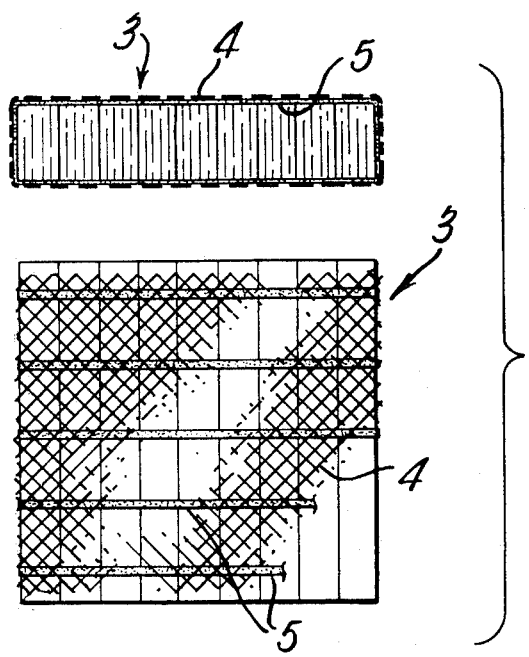
Figure 3:
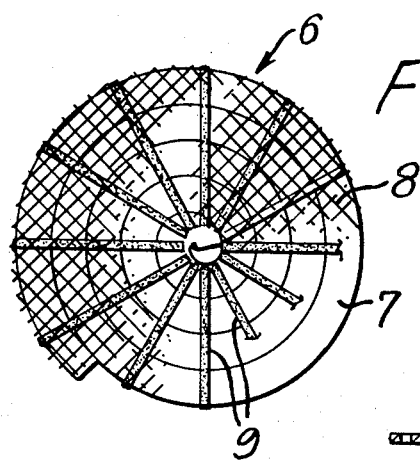
Figure 4A:
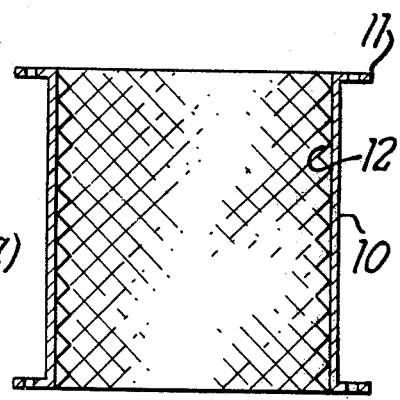
Figure 4B:
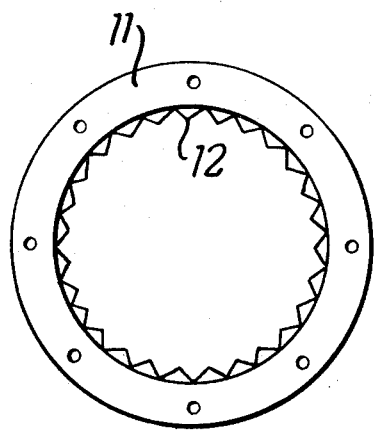
Figure 4C:
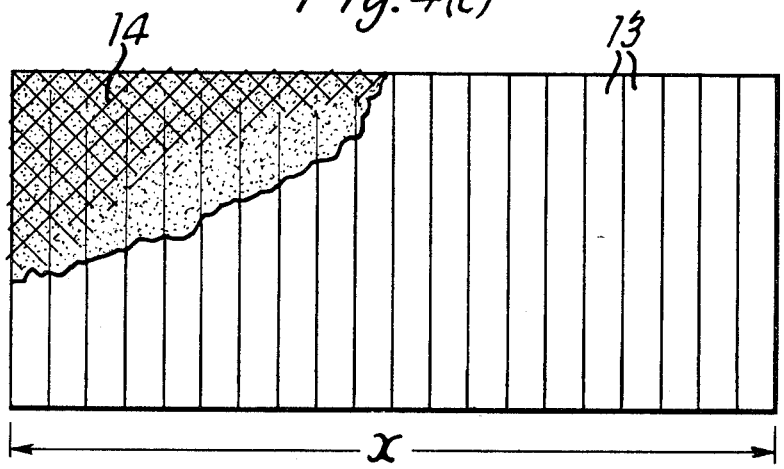
Figure 4D:
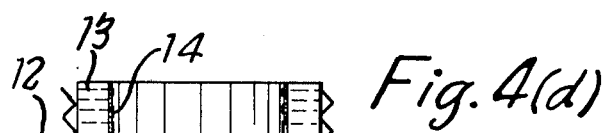
Figure 4E:
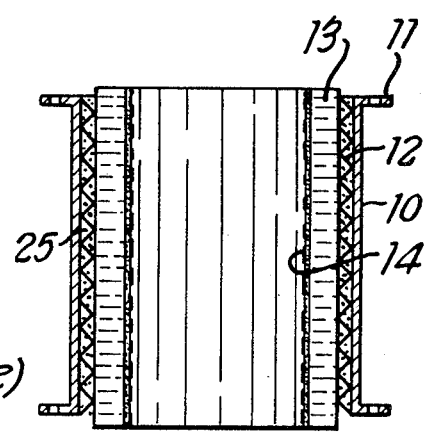

Various embodiments of the invention will now be described in the accompanying drawings wherein:

FIG. 1 is a diagrammatic view in section and a fragmentary plan illustrating a biscuit in accordance with the invention;

FIG. 2 in section and in plan illustrates the netting wrapping of a biscuit; and FIG. 3 in plan illustrates a circular biscuit.

Referring now to FIG. 1 a biscuit 3 typically 225 mm square and 50 mm thick made up of strips 3a of "end-on" fibres is secured to a furnace wall 1 by a layer 2 of cement. The end-on configuration of individual fibres is diagrammatically illustrated by the shading. The plan view illustrates how the end-on fibre strips 3a are preferably orientated in an array of biscuits so that no continuous composite strips are defined.

FIG. 2 shows a biscuit wrapped in netting 4 by a strip-shaped bonding layer 5 of organic glue, i.e., combustible to dissipate as gaseous products.

FIG. 3 shows a circular biscuit 6 formed by winding a strip 7 of end-on pieces into a circular structure somewhat similar in shape to a large 'Catherine Wheel' firework. The wound strip is wrapped in netting 8 secured by radially strip shaped bonding layers 9 of glue.

German laid open Pat. No. 2,513,740 (Zirconal Processes Limited) and British Pat. No. 1,427,708 (Zirconal Processes Limited) disclose useful binder/accelerator systems while British Pat. No. 1,423,167 discloses a cement for sticking ceramic fibres.

FIG. 4 of the accompanying drawings shows the application of the invention to the lining of a flue made up of a plurality of metal cylindrical sections 10 joined end to end. To facilitate joining each end of each section 10 has an annular radially outwardly extending flange 11 (FIGS. 4(a) and 4(b)). A sheet 12 of expanded metal mesh is formed into a cylinder to fit the internal diameter of the section 10, the butting edges of the sheet being tack welded together to form the cylinder. Strips 13 of ceramic fibre are laid transversely on a broad strip of netting 14, the strips 13 being secured to the netting 14 with organic glue (FIG. 4(c)). Each strip 13 is formed of fibres in the "end-on" orientation as previously described so that in use of fibres extend radially inwardly in use. The length of the netting, i.e., the distance X equals the internal circumference of the expanded metal sleeve 12 whilst the width of the netting, i.e., the length of the strips 13 is slightly longer than the length of the section. The netting 14 carrying the strips is formed into a cylinder this having the effect of compressing the inner parts of the ceramic fibre strips 13 and the sleeve thus formed FIG. 4(d) is inserted into the metal sleeve. The external surface of the composite metal mesh and fibre sleeve thus formed is then coated with refractory cement 25 and inserted into the flue section to produce the assembly shown in FIG. 4e. When adjacent assemblies are secured together end on by the flanges 11 projecting fibre strips 13 are compressed together.

Figure 5:
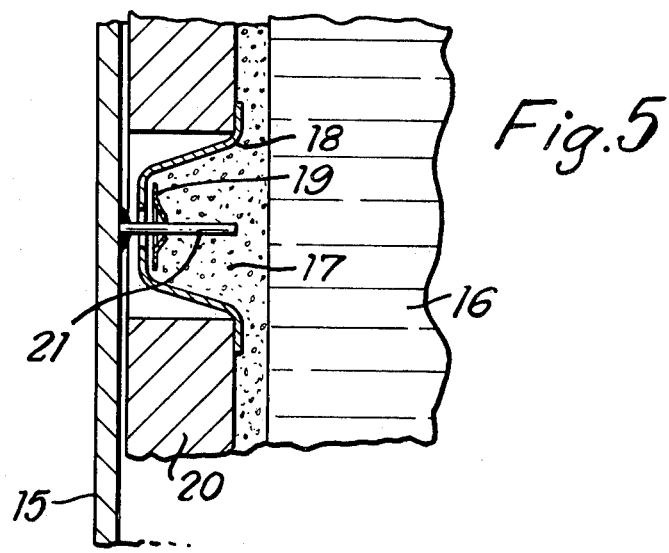

FIG. 5 of the accompanying drawings shows the invention as applied to building up a furnace wall on a steel casing 15. Here in addition to the module 16 applied with a tacky cement layer 17 in accordance with the invention an intermediate layer of insulating material is applied. Thus specifically the steel casing 15 has pinned thereto using suitable pins 21 anchors 18 and washers 19 insulating block material 20. In the described and illustrated embodiment the insulating blocks 20 are discrete items having sufficient integrity to be fixed in the manner described. When the supplementary insulating material lacks such physical integrity and is for example mineral wool it can be wrapped for example in expanded metal sheet and either anchored or cemented in position.

Examples of compositions hardenable by an acid producing gas and suitable for use according to the present invention are as follows:

| Composition No. 1 | |
|---|---|
| Potassium silicate solution 'Pyramid' No. 53 This solution has the following properties: Wgt.ratio $SiO_2$: $K_2O$ 2.48:1 Mol.ratio $SiO_2$: $K_2O$ 3.89:1 $SiO_2$ = 21.30% w/w $K_2O$ = 8.60% w/w | 100 grams |
| Aminoalcohol | 10 grams |
| 'Molochite' (Sintered China Clay) - 120 grade | 100 grams |
| Mica | 10 grams |
| Tabular alumina - 24 & 48 grade | 15 grams |

The addition of the tabular alumina is not essential. The aminoalcohol is monoethanolamine or tris (hydroxymethyl) methylamine. It may, if desired, be replaced by 10 ml of aqueous ammonia solution sp.gr. 0.88.

| Composition No. 2 | |
|---|---|
| 'Claysil' No. 1 (Claysil is a dispersion of clay in sodium silicate solution having the following properties: Wgt. ratio $SiO_2$: $Na_2O$ 3.30:1 Mol. ratio $SiO_2$: $Na_2O$ 3.41:1 $Na_2O$ = 6.57% w/w $SiO_2$ = 21.70% w/w Total solids = 51.1% w/w Viscosity at 20° C. 250-1200 centipoises | 100 grams |
| Ammonia solution 0.88 sp.gr. | 10 ml |

The invention will now be described with reference to the attachment of ceramic fibre thermal insulation to a furnace wall. It is essential to use only a thin layer of a composition such as composition No. 1 or No. 2. The furnace wall is coated with a thin layer, thickness about 0.1 inch, with Composition No. 1 or Composition No. 2. Strips of ceramic fibre, oriented so that a substantial proportion of the fibres are end-on to the supporting surface, are embedded in the composition, which is now hardened by the action of carbon dioxide gas.

"Biscuits" suitable for use in the furnace wall construction may be supplied with the hot face protected by corrugated cardboard and the sides protected by paper. The reverse or cold face may also be covered wholly or in part by a backing material, to retain the shape during transit or insulation, or to form a key with the cement. A suitable backing material is glass fibre, covering about 20% of the area of the cold face. Either cold face or furnace wall may be coated with the compositions, or both may be coated.

Figure 6:
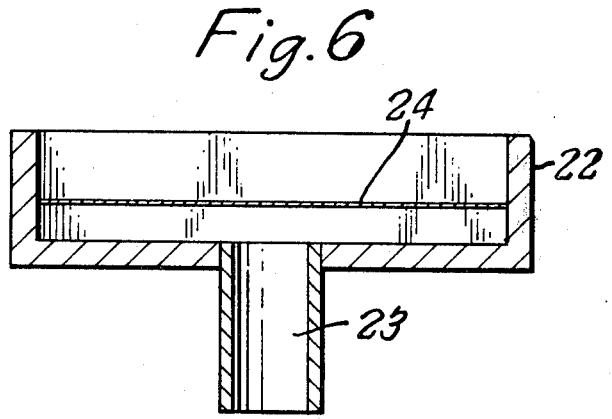

FIG. 6 of the accompanying drawings shows a tool suitable for use in attaching a "biscuit" to a furnace wall. The tool comprises a box 22 made of light gauge metal, to accept a "biscuit" as an easy fit, with a hollow tube 23 to function as a handle and as an inlet for carbon dioxide gas. A light gauge metal plate 24 can be provided to locate the biscuit. The biscuit is placed on the box, with the cold face uppermost, then a thin layer of Composition No. 1 or No. 2 is applied. After cement coating, the biscuit is located in the required tubes, which pass through the fibres and make contact with the cement composition. The inlet tube for carbon dioxide gas is above this plate.

In the following examples, the tacky rear surface layer mentioned previously is one of the compositions described in U.K. Pat. No. 1,423,167. Of the compositions described in U.S. Pat. No. 1,423,167 those using Laponite SP are preferred. In the following, these cmpositions will be referred to as "sol cements", for convenience.

EXAMPLE A

Sol cement was applied to a furnace insulating brick (hot face) and to a group of ceramic fibre strips constituting a module. Zirconium acetate solution was poured over both cement surfaces, then the surfaces were immediately joined. Three minutes after the surfaces were joined the cement had set. The adhesion between brick and ceramic fibres was good.

No advantage was gained by first treating the fibre strips with zirconium acetate solution, then applying the sol cement to the surface of the fibres, followed by pouring zirconium acetate solution over the cement. Priming the brick surface with zirconium acetate solution gave no advantage.

EXAMPLE B

The tacky rear surface layer was formed by immersing the ceramic fibre strips in zirconium acetate solution. A layer of sol cement was applied to a furnace insulating brick. Then the ceramic fibre strips (impregnated with zirconium acetate solution) were applied to the layer of sol cement. The cement set in about 3 minutes after the surfaces were joined, but the adhesion was not so good as in (A). The zirconium acetate solution used in (A) and (B) contained 20% $ZrO_2$ w/w.

A suitable zirconium acetate solution is described in British Aluminum Company's data sheet No. 431.

EXAMPLE C

An alternative to zirconium acetate solution is an acid hydrolysed ethyl silicate solution. The preparation of a suitable acid hydrolysed ethyl silicate solution is described in British Pat. No. 1,356,249.

Sol cement was applied to a furnace insulating brick and to a group of ceramic fibre strips. Acid hydrolysed ethyl silicate solution was poured over both cement surfaces, then the surfaces were immediately joined. The cement had set three minutes after the surfaces were joined. The adhesion between brick and ceramic fibres was good and improved on standing.

An alternative procedure is to apply the sol cement to the surface of the ceramic fibre, then place the coated surface on the wall of an existing furnace. The cement is hardened by applying zirconium acetate solution or acid-hydrolysed ethyl silicate solution to the cement surface. A "grease gun" is suitable for this.

The sol cement may be hardened by physical means, for instance by application of local heat. One way of applying local heat is to embed a heating element in the cement. This heating element can conveniently be made from an electric resistance wire suitable for operating at high temperature. "Nichrome" wire is suitable.

What is claimed is:

1. In a method for reducing the thermal inertia of a furnace or wall oven by lining the oven with refractory fibers disposed with their ends end on to the wall, the improvement comprising
    (i) compressing a plurality of modules of said refractory fibers disposed with one end, end on to the plane of one end of the modules, by wrapping the compressed modules in a thermally combustible material;
    (ii) applying the modules side by side to a furnace or oven wall;
    (iii) firing the furnace or oven to thermally destroy the wrapping material and release the modules from compression thereby causing each module to press against adjacent modules.

2. Method of claim 1 wherein the combustible material is combustible netting.

3. Method of claim 1 wherein the modules are applied to said wall by coating the rear of each module with an adhesive substance, causing or allowing the said substance to become tacky, applying the module to said wall so that the module is supported against gravity by the tacky substance and causing or allowing the tacky substance to set into a stable heat-resistant and refractory condition thereby firmly fixing the modules to the wall.

4. Method of claim 3 wherein the tacky substance is contacted with a reagent, either before or after application to the furnace wall, which causes it to set.

5. Method of claim 4 wherein the module is coated with an adhesive substance which, immediately prior to placing the module, is treated with a setting agent.

6. Method of claim 4 wherein the tacky module is applied to the surface and subsequently caused to set by the introduction of the setting agent.

7. Method of claim 3 wherein the tacky substance is caused to set by heat, electrical, microwave or ultrasonic energy.

8. Method of claim 7 wherein the energy is applied by appropriate electrodes.

9. Method of claim 1 wherein the fibres are ceramic fibres.

10. Method of claim 1 which includes the step of applying an intermediate layer of insulating material prior to applying said modules.

11. Method of claim 1 wherein the module is circular and formed by winding a strip of fibrous material into a spiral.

12. Method of claim 1 wherein the modules are first applied to a deformable former which is bent into a cylindrical shape and inserted into a flue to be lined.

13. The method of claim 1 wherein said module is totally wrapped in said wrapping material.

14. In a module for application to a furnace or oven wall to reduce the thermal inertia thereof and having refractory fibers with one end end on to the plane of one end of the module, the improvement comprising a wrapping of thermally combustible material which on first firing of the furnace or oven is thermally destroyed, said wrapping being disposed about said module to hold said module in elastic compression whereby, when said wrapping is thermally destroyed, said module is released from compression and free to expand.

15. The module of claim 14 wherein said wrapping material is a netting wrap.

* * * * *